(12) United States Patent
Schuman

(10) Patent No.: US 8,409,069 B1
(45) Date of Patent: Apr. 2, 2013

(54) BRACHYTHERAPY APPLIANCE AND METHOD

(76) Inventor: Ethan J. Schuman, University City, MO (US)

( * ) Notice: Subject to any disclaimer, the term of this patent is extended or adjusted under 35 U.S.C. 154(b) by 721 days.

(21) Appl. No.: 11/453,769

(22) Filed: Jun. 15, 2006

(51) Int. Cl.
*A61M 36/04* (2006.01)

(52) U.S. Cl. ................................. 600/3; 600/7

(58) Field of Classification Search .................. 433/215, 433/219; 128/859, 861; 607/134; 600/1–8
See application file for complete search history.

(56) References Cited

U.S. PATENT DOCUMENTS

| | | | | |
|---|---|---|---|---|
| 1,455,476 | A * | 5/1923 | Cameron | 600/3 |
| 2,151,738 | A * | 3/1939 | Buhse | 604/20 |
| 3,380,446 | A * | 4/1968 | Martin | 601/2 |
| 3,667,454 | A * | 6/1972 | Prince | 601/18 |
| 3,872,856 | A * | 3/1975 | Clayton | 600/6 |
| 4,144,882 | A * | 3/1979 | Takemoto et al. | 604/22 |
| 5,190,990 | A * | 3/1993 | Eichmiller | 523/137 |
| 5,653,683 | A * | 8/1997 | D'Andrea | 604/21 |
| 5,792,067 | A * | 8/1998 | Karell | 600/534 |
| 5,840,008 | A * | 11/1998 | Klein et al. | 600/3 |
| 6,061,588 | A * | 5/2000 | Thornton et al. | 600/424 |
| 6,238,687 | B1 | 5/2001 | Mao et al. | 424/426 |
| 6,361,487 | B1 * | 3/2002 | Green et al. | 600/7 |
| 6,400,796 | B1 * | 6/2002 | Munro et al. | 378/64 |
| 6,514,191 | B1 * | 2/2003 | Popowski et al. | 600/3 |
| 6,540,655 | B1 * | 4/2003 | Chin et al. | 600/3 |
| 6,582,352 | B2 | 6/2003 | Verin et al. | 600/1 |
| 6,616,629 | B1 | 9/2003 | Verin et al. | 604/101.05 |
| 6,733,485 | B1 | 5/2004 | Whitehurst et al. | 604/500 |
| 6,901,294 | B1 | 5/2005 | Whitehurst et al. | 607/39 |
| 6,901,296 | B1 | 5/2005 | Whitehurst et al. | 607/50 |
| 7,048,698 | B2 * | 5/2006 | Whalen et al. | 600/587 |
| 2004/0116767 | A1 * | 6/2004 | Lebovic et al. | 600/7 |
| 2005/0080313 | A1 * | 4/2005 | Stewart et al. | 600/3 |
| 2005/0101823 | A1 * | 5/2005 | Linares et al. | 600/3 |
| 2005/0124843 | A1 * | 6/2005 | Singh | 600/3 |
| 2006/0020156 | A1 * | 1/2006 | Shukla | 600/3 |
| 2006/0100475 | A1 * | 5/2006 | White et al. | 600/3 |
| 2006/0116546 | A1 * | 6/2006 | Eng | 600/3 |
| 2006/0171506 | A1 * | 8/2006 | Lovoi et al. | 378/130 |

OTHER PUBLICATIONS

Ariji E, Customized mold brachytherapy for oral carcinomas through use of high-dose-rate remote afterloading apparatus. Oral Surgery, Oral Medicine, Oral Pathology, Oral Radiology, and Endodontics 87(4): 508-12, Apr. 1999.*
Ngan RKC, Interstitial Brachytherapy for Early Oral Tongue Cancer Using Iridium Hairpin or Wire. J HK Coll Radiol 7:88-94, 2004.*

(Continued)

*Primary Examiner* — Charles A Marmor, II
*Assistant Examiner* — Catherine E Burk
(74) *Attorney, Agent, or Firm* — Matthews Edwards LLC

(57) ABSTRACT

A brachytherapy appliance and method utilizing a body portion or element removably positionable within a cavity of a living body, such as an oral cavity, the body portion having a shape at least generally conforming to a surface within the cavity in proximity to a cancer or diseased tissue so as to be retainable in intimate relation with the surface, and at least one conduit in connection with the body portion and extending to a predetermined location adjacent to the cancer when the body portion is retained in the cavity, the at least one conduit being adapted for cooperatively receiving a radiation emitting element or media for positioning the radiation emitting element or media at the predetermined location adjacent to the cancer for irradiating the cancer, and at least one radiation shield in association with the body portion adapted for shielding adjacent tissue and/or organs from radiation emitted by the radiation emitting element or media.

22 Claims, 5 Drawing Sheets

OTHER PUBLICATIONS

Prisciandaro J, A buccal mucosa carcinoma treated with high dose rate brachytherapy. Journal of Applied Clinical Medical Physics 6(1): 8-12, Winter 2005.*

Harrison L, Applications of Brachytherapy in Head and Neck Cancer. Seminars in Surgical Oncology 13:177-184, 1997.*

* cited by examiner

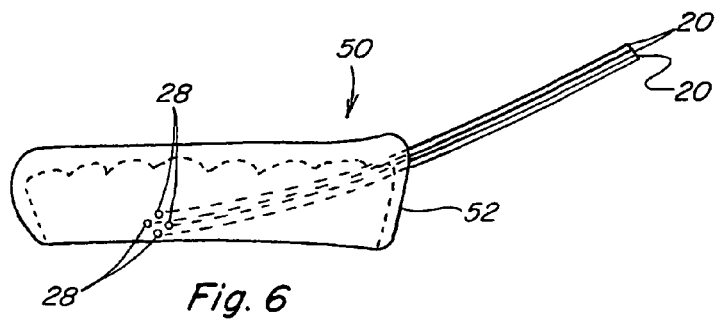
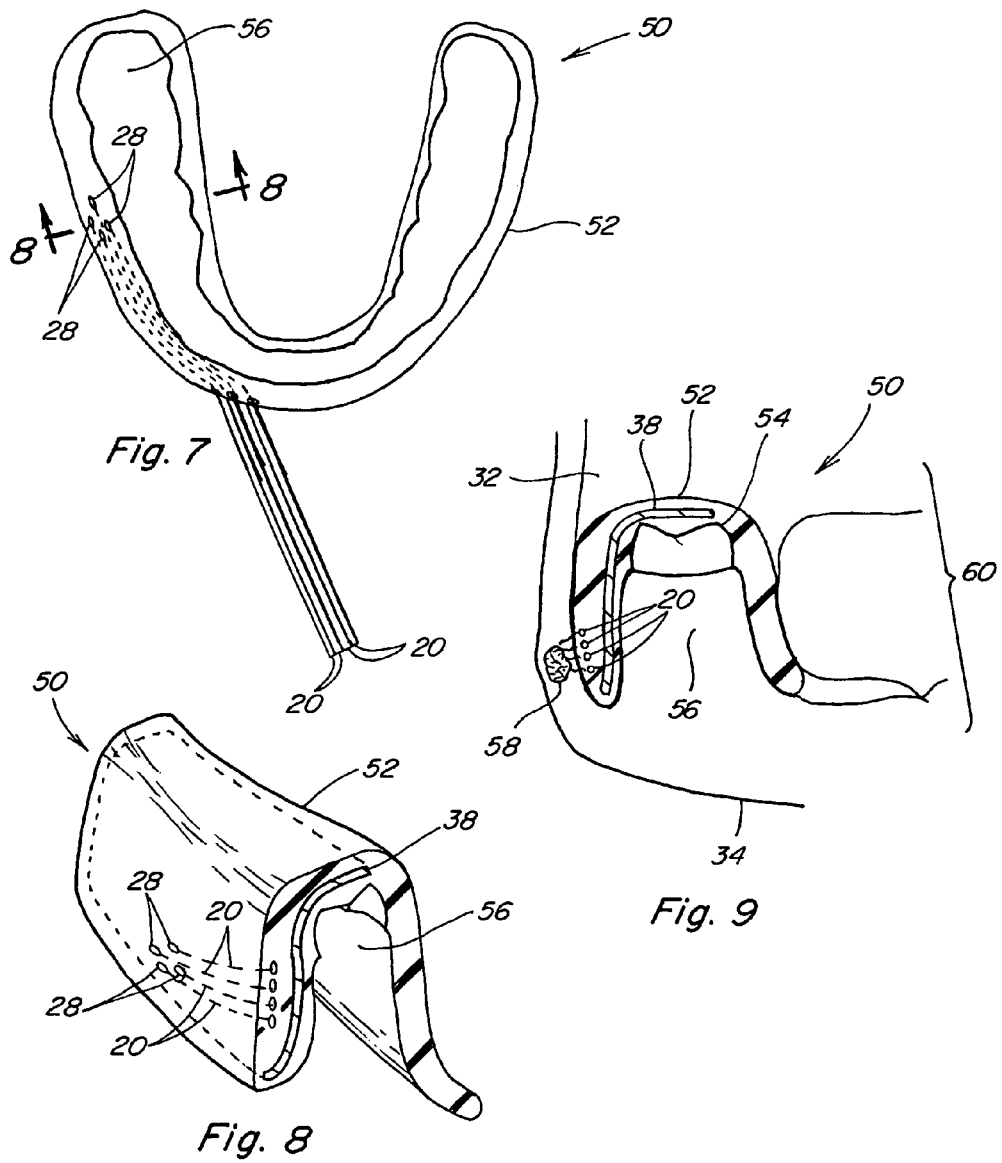

BRACHYTHERAPY APPLIANCE AND METHOD

TECHNICAL FIELD

This invention relates generally to appliances positionable in a cavity of a living body, such as the body of a human or animal, for removably positioning a therapeutic device in a desired precise location in relation to a selected portion of the body in or adjacent to the cavity, and, more particularly, the invention relates to a brachytherapy appliance positionable and retainable in the oral cavity for holding one or more radiation therapy delivery elements in desired relation to a cancer, tumor, or other diseased tissue, for irradiating it, while shielding adjacent healthy tissue regions from the radiation, and a method of practicing the same.

BACKGROUND OF THE INVENTION

In the field of medicine, there are courses of treatment for diseases and injuries which are facilitated by placement of a therapeutic device within a body cavity, in a particular relation to a selected, or a predetermined, region thereof, or adjacent tissue, for delivering a therapeutic dosage. For instance, in oncology, particularly for the treatment of mouth and/or throat cancers, and more generally cancers of the head and/or throat, breast and prostate, and also non-cancerous diseases, such as non-malignant tumors and neuromas, therapeutic benefit has been achieved by brachytherapy, that is, the placement of radioactive elements, also referred to as radioactive seeds, in proximity to, or surgically directly in the cancer or cancerous or other diseased tissue, for directing radiation thereat. However, a side effect that has been observed is relatively uncontrolled irradiation of the surrounding tissue and/or organs. Specifically in this regard in relation to cancers and other diseases of the neck, head and mouth, is injury to and loss of teeth, and injury to salivary and other glands such as those relating to the sense of taste and smell, which is undesirable for many reasons.

It is thus sought to provide an appliance configured and/or adapted for placement within a body cavity, such as, but not limited to, the oral cavity, which allows removably or temporarily positioning of one or more radiation emitting elements, such as radioactive seeds, wires or the like, in precise relation to a cancer or other diseased tissue in or adjacent to the cavity, which provides shielding for other regions of healthy tissue, glands and/or organs, as well as teeth, from the radiation emitted by the radioactive element or elements. Further in this regard, it would be advantageous to provide an appliance custom configured, such as by molding, to conform to the shapes and contours of certain tissue regions defining a body cavity, so as to be positionable and automatically retained thereagainst in conforming relation thereto in a selected precise location and orientation in relation to the tissue which is to be irradiated, while providing radiation shielding for the other tissue and organs not intended to be irradiated. In such appliance, it would be advantageous to provide at least one receptacle or passage into which a therapeutic device, such as a seed or seeds, or a wire having a radioactive tip or other region, or other radioactive medium, is removably insertable, so as to be positioned for delivery of a radioactive dose in precise relation to a cancer to be irradiated for a specific time or specific therapeutic dosage.

SUMMARY OF THE INVENTION

According to the invention, a brachytherapy appliance and method of practicing the same, which overcomes one or more of the problems and/or shortcomings, and provides one or more of the advantages set forth above, is disclosed.

According to a preferred aspect of the invention, a brachytherapy appliance is provided including a body portion fabricated to conform to interior surface contours of a body cavity, particularly the oral cavity, so as to be insertable into the cavity and positioned in close proximity to or against the interior surface soon as to be retained in the cavity, the body portion including at least one receptacle or passage disposed in or extending through a portion thereof adapted for receiving and holding a therapeutic element in precise relation to a cancer or cancerous tissue in the cavity or in nearby tissue, and shielding for protecting other tissue and body portions from the therapeutic element or effects thereof, particularly radiation therefrom. The invention additionally includes a therapeutic element, which can be for instance, but is not limited to, a radiation delivery element such as a wire including a radiation emitting or irradiated portion, such as a tip or other segment, or one or more radiation emitting seeds, or other radioactive media, which is removably insertable in the body portion receptacle or passage in a predetermined position and/or orientation for emitting radiation toward the cancer or cancerous tissue. By providing the radioactive media separately of the body portion, the number and radioactivity of the radioactive media can be varied, for instance, to allow changing the radiation dose or time of dosage over the course of therapy, or otherwise. This also allows use of the same radioactive media with more than one appliance, and also facilitates handling and storage of the radioactive media, and safe disposal of the non-radioactive body portion.

According to another preferred aspect of the invention, the body portion is configured or custom fit to fit securely on the upper teeth in the oral cavity, if any, or to the upper edentulous arch, such as by molding, so as to be positioned in the superior region of the oral cavity. The body portion is fabricated from a suitable polymeric material, such as, but not limited to, a suitable well known, commercially available moldable dental acrylic, such as, but not limited to, a methyl methacrylate. The at least one receptacle or passage will be molded into the body portion, and will comprise a tube or catheter adapted for receiving the radiation emitting media, such as a wire, therein, the tube or catheter being routed so as to have a portion or opening positioned to be disposed in desired relation to the cancer when the body portion is properly positioned in the body cavity, for delivery of the desired therapy, i.e., irradiation and destruction of the cancerous or diseased tissue or cells. The body portion additionally includes one or more layers of shielding material embedded therein, such as a lead shielding material, positioned for shielding adjacent healthy tissue, organs, teeth, or other vulnerable body parts, from radiation emitted by a radioactive region or portion of a wire or other radiation emitting media inserted into the tube or catheter. The lead shielding material, in turn, is incorporated into the body portion such that when the body portion is positioned in the oral cavity, the lead material will not contact the adjacent tissue, nor will the lead material be exposed to saliva or other fluids present in the cavity, which could carry contaminants to the surrounding tissue. It is also contemplated that an appliance of the invention can be configured for fitting in other regions of the oral cavity, such as on the lower teeth and/or edentulous arch, for treatment of cancers or diseases in the vicinity thereof.

According to still another preferred aspect of the invention, the radiation emitting media comprises a wire removably insertable into the tube or catheter, and can be, for instance, a stainless steel wire, and can be, for instance, tipped with iridium 192, or another suitable radioactive substance. The wire is of a suitable length so as to extend through the tube or catheter so as to position the irradiated portion in the desired location in relation to the cancer or other diseased tissue, hereinafter sometimes referred to as "the cancer", with the opposite end of the wire protruding from the appliance, and more preferably, also from the body cavity so as to be graspable for insertion and removal from the appliance. The wire can also include indicia along the length thereof for indicating proper placement of the tip or other irradiated portion at the desired location within the appliance, and thus in relation to the cancer to be irradiated.

According to a further preferred aspect of the invention, the body portion of the appliance will include multiple ones of the tubes or catheters, as required for holding the media necessary for irradiating the cancer to the desired extent. As an example, a plurality of the tubes or catheters will be arranged in a required array, such as, a linear, side-by-side array, for providing a desired pattern and/or dose of radiation to the cancer. The required location of the tubes or catheters within the body portion of the appliance will be determined by the location of the cancer or diseased tissue, as found using common techniques, such as CT scanning or the like. The duration and/or dosage of treatment will be determined by an oncology professional or physicist.

According to a still further preferred aspect of the invention, a method of use of the appliance will include steps of molding the body portion to a region of a body cavity, such as the oral cavity, including installing the shielding and the at least one tube or catheter in the respective locations for holding the radioactive media for providing the radiation dosing to the cancer. The finished appliance can then be inserted into the oral cavity and secured in place. The radioactive wire or wires or other media are then inserted into the one or more catheters or tubes, respectively, to position the radioactive element or elements in the desired relation to the cancer or diseased tissue. The appliance will then be left in place for the period of time necessary for delivery of the determined radiation dose to the cancer or diseased tissue. The radioactive wire or wires are then removed from the appliance, and the appliance removed from the oral cavity.

BRIEF DESCRIPTION OF THE DRAWINGS

FIG. 6 is a side view of aspects of another brachytherapy appliance according to the present invention, including a plurality of catheters for receiving radioactive tipped wires, respectively, for dosing a cancer with radiation;

FIG. 7 is a bottom view of the brachytherapy appliance of FIG. 6;

FIG. 8 is a sectional view taken along line 8-8 of FIG. 7; and

FIG. 9 is another sectional view of the appliance of FIGS. 6 and 7, illustrated in association with teeth and a jaw in an oral cavity of a human head.

DETAILED DESCRIPTION OF PREFERRED EMBODIMENTS

Figure 1:
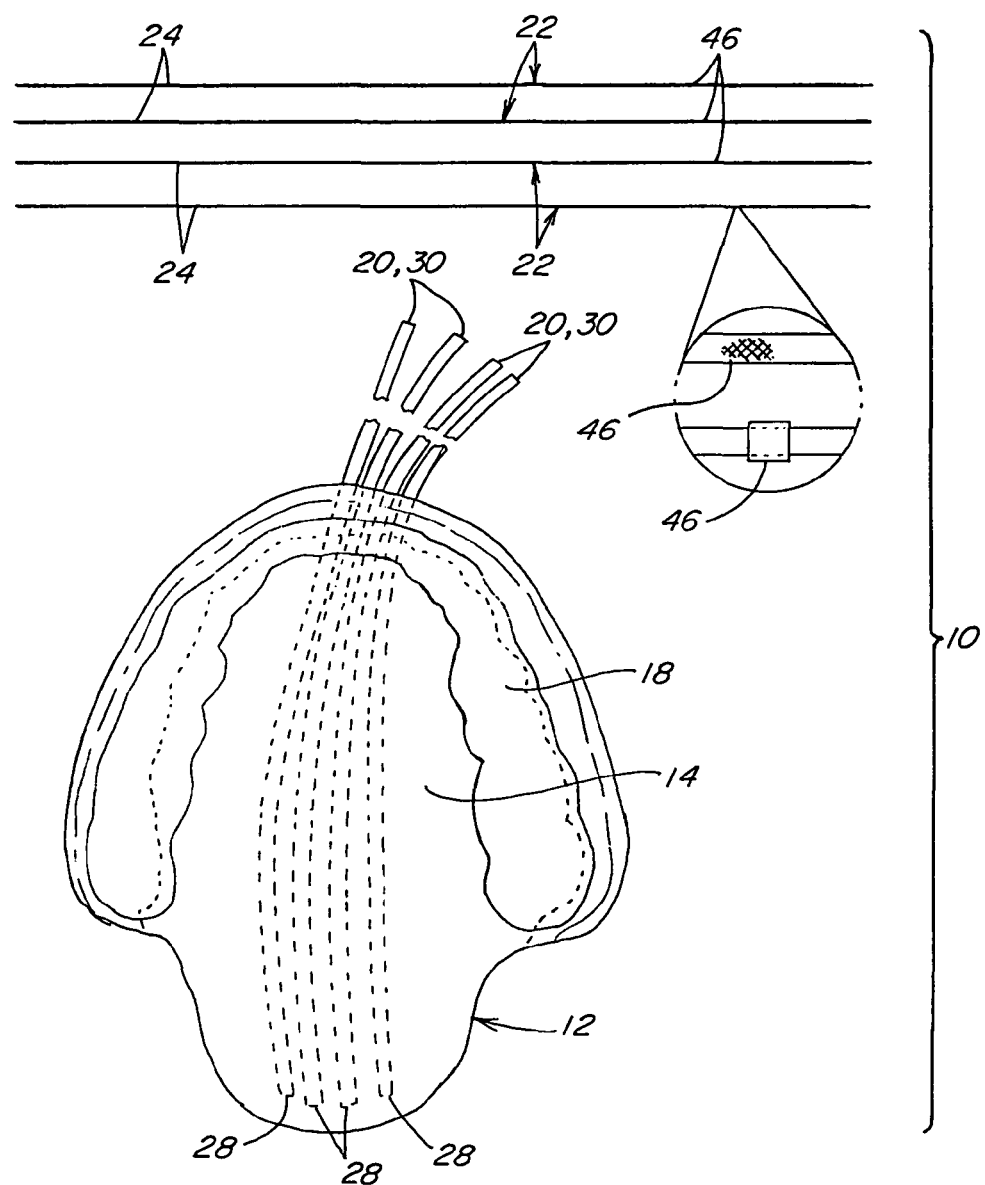
FIG. 1 is a top view of aspects of a brachytherapy appliance according to the present invention, including a plurality of catheters for receiving radioactive tipped wires, respectively, for dosing a cancer with radiation.

Referring now to FIGS. 1, 2, 3 and 4, wherein like numerals refer to like parts, a brachytherapy appliance 10 constructed and operable according to the teachings of the present invention, is shown. Brachytherapy appliance 10 is configured for use in an oral cavity of a living body, which, as depicted hereinafter, is a human body. Appliance 10 generally includes a body portion 12 which will be at least generally and preferably custom molded to the contours of a region of an oral cavity of a living body. More particularly, body portion 12 is molded to conform to the upper regions or palate of a human oral cavity, including a center region 14 molded to selected regions of the hard and/or the soft palate of the oral cavity, and a peripheral region 16 molded to the upper teeth, if any, and/or the endentulous ridge or arch, thereby forming a recess 18 extending partially around the center region 14, and contoured for cooperatively receiving and releasably attaching to the upper teeth, if any, or to the edentulous ridge or arch. Body portion 12 can be molded using common dental molding techniques and commercially available polymeric materials commonly used in the same, such as a well-known, commercially available dental acrylic material such as a methyl methacrylate. Importantly, at least one therapy delivery element is incorporated into appliance 10, which here preferably comprises at least one catheter 20 incorporated in or on body portion 12. Each catheter 20 is preferably adapted for cooperatively receiving and positioning radioactive media in desired relation to a cancer, which media here comprises an elongate wire 22 including a radiation emitting portion, which is preferably a radioactive tip 24 of iridium 192. Each catheter 20 is essentially a hollow tube defining a passage 26 (FIG. 4) having at least a terminal end portion 28 (FIG. 1) which is precisely positioned in relation to body portion 12, such that when a wire 12 is received in passage 26 with radioactive tip 24 located in the terminal end portion 28, tip 24 will be precisely positioned for irradiating a cancer or diseased tissue when appliance 10 is installed in the oral cavity.

Figure 5:
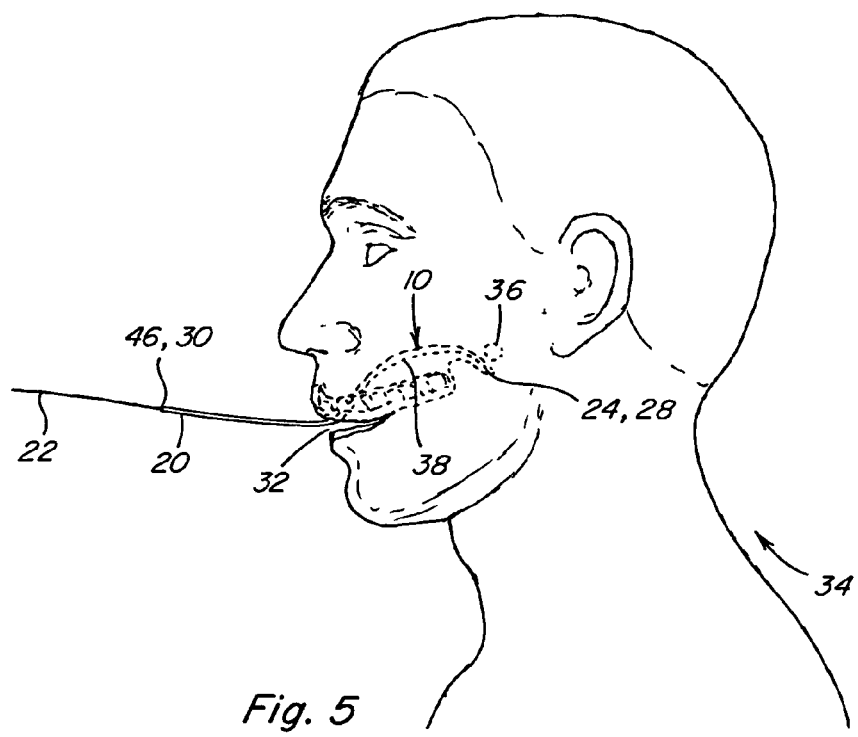
FIG. 5 is a side view of a human head including a brachytherapy appliance of the invention installed in an oral cavity of the head.

The location, size and extent of the cancer will be determined by an oncology professional, and the radiological dosing will be determined by the oncology professional and/or physicist. From that information, the number and position of catheters 20 required will be determined by the professionals. Appliance 10 will be fabricated to include the required number of catheters 20, in the required position or positions, such that the therapy delivering region or regions of the wire or wires inserted into the catheter or catheters will be properly disposed for delivering the contemplated radiation dose to the cancer or diseased tissue. In this embodiment, this will entail the positioning of terminal end portions 28 of the catheters 20 in, or in connection with, molded body portion 12, such that the radioactive tips 24 of the wires when located in the catheters will be positioned for delivery of the required radiation dose to the cancer. Preferably, this will entail the fixed molding in place of catheters 20 within body portion 12, such that terminal end portions 28 will be fixed in location with respect to the cancer or diseased tissue when appliance 10 is installed in the oral cavity. Also preferably, this will entail allowing the extension of opposite ends 30 of catheters 20 from body portion 12, and thus also from the mouth 32 of a person 34 when appliance 10 is installed, as shown in FIG. 5. This will allow a healthcare professional to safely and conveniently insert wires 22 into catheters 20 with body portion 12 installed in the mouth, to position radioactive tips 24 at terminal end portions 28 within catheters 20, for delivering the required radiation dose to a cancer or diseased tissue, such as representative cancer 36, also illustrated in FIG. 5. At the end of the radiation therapy, wires 22 are removed from body portion 12, and body portion 12 removed from the mouth.

As noted hereinabove, radiation emitted by a therapeutic device, such as any of radioactive tips 24 of wires 22, can potentially unintentionally injure or damage noncancerous body parts, tissue, glands and/or organs, such as the teeth, salivary glands, olfactory nerves, taste buds, and the like. To avoid such injury or damage, appliance 10 includes one or more shields, such as a radiation shield 38 as variously illustrated in FIGS. 4, 4a, 4b, 4c and 4d, in association with body portion 12, positioned or disposed for providing shielding of desired tissue regions, glands, organs, and/or other body parts, from radiation emitted by tips 24. A shield, such as radiation shield 38, can comprise a suitable radiation absorbing or containing material, such as lead. To protect non-diseased body portions, such as the tissue of the superior region of the oral cavity, such as the endentulous arch, the tongue, teeth, and the like, located in the vicinity of a shield, such as shield 38, from unhealthy effects from exposure to the material of the shield, the shield is preferably encapsulated by a layer of protective material, for instance, by one or more layers of the polymeric material constituting body portion 12, such as an acrylic or the like. A shield can be encapsulated within body portion 12 when molded, or can be installed on a surface thereof, then coated with the protective layer. Here, for instance, terminal and portions 28 of catheters 20 are disposed in the posterior region of body portion 12, for irradiating a cancer in the posterior region of the oral cavity, or the upper throat region, as generally illustrated by cancer 36 in FIGS. 5 and 5a. Shield 38 for this location, can cover the inferior or lower or lateral surface of body portion 12 which will face the oral cavity, generally denoted as region 40 in FIG. 3, to protect the healthy tissue, as well as those portions of the upper teeth and gums that face and therefore could be injured by subjection to radiation emitted by tips 24 when installed in catheters 20 (FIG. 5a), as generally denoted by regions 42 and 44 in FIG. 4.

Here, it should be noted that it is contemplated that the shielding to be used in association with a brachytherapy appliance of the invention, such as appliance 10, can take any of a variety of forms, as desired or required for providing protection to tissue and other body parts from radiation emitted by the radioactive elements of the appliance. For instance, the shielding can take the form of an envelope (FIGS. 4a, 4b, 4c and 4d) covering both the superior and/or inferior surfaces of catheters 20, as well as, anterior and/or posterior shielding and lateral shielding. More particularly in this regard, it is contemplated that an appliance according to the invention could include catheters 20 which are substantially completely ensconced within radiation shielding, with the exception of one or more precisely placed and oriented windows, such as a window or windows 48 (FIGS. 4b, 4c and 4d) for the emission of radiation toward a cancer or diseased tissue.

Figure 2:
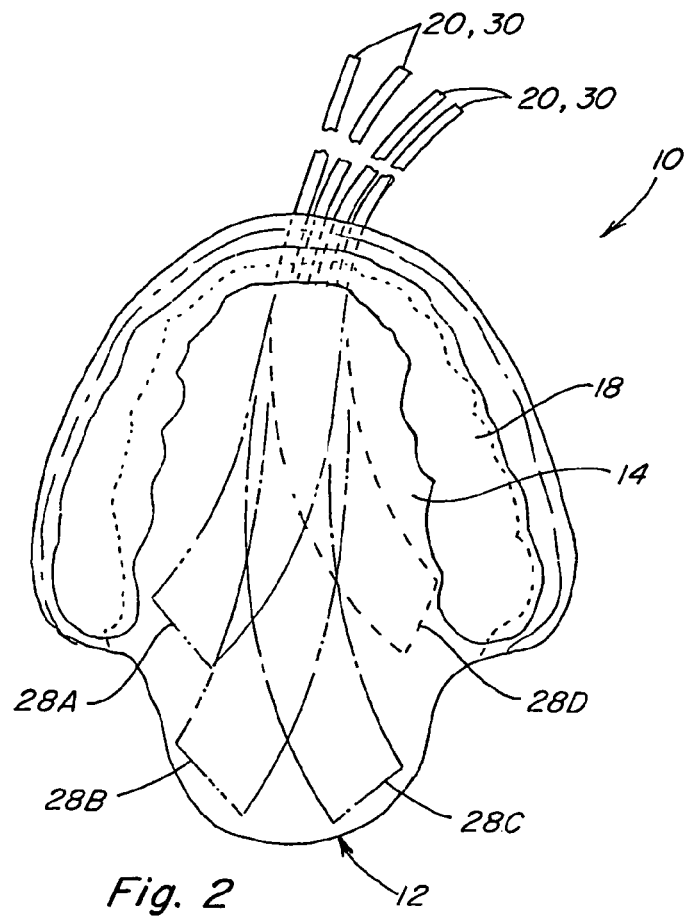
FIG. 2 is another top view of the brachytherapy appliance, illustrating alternative locations for the catheters.
Figure 3:
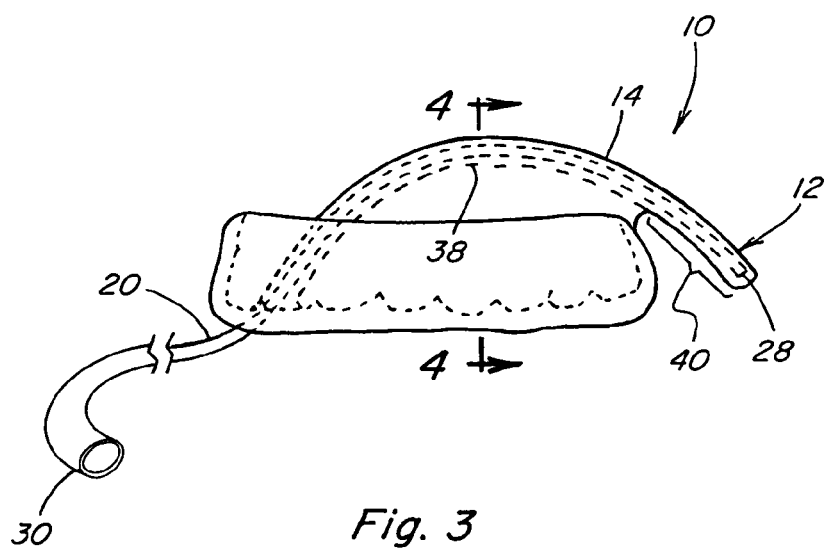
FIG. 3 is a side view of the brachytherapy appliance.

Referring more particularly to FIG. 2, as noted above, it is also contemplated that catheters 20, and more particularly, the terminal end portions 28 or other portions thereof which are to hold the radiation emitting elements, can be positioned at any location on or in connection with an appliance of the invention, such as appliance 10, for facilitating delivery of the radiation dose required for treatment of a cancer. This is denoted by numerals 28A, 28B, 28C and 28D, which illustrate alternative locations for terminal and portions 28, both in the anterior/posterior and lateral directions.

Figure 4:
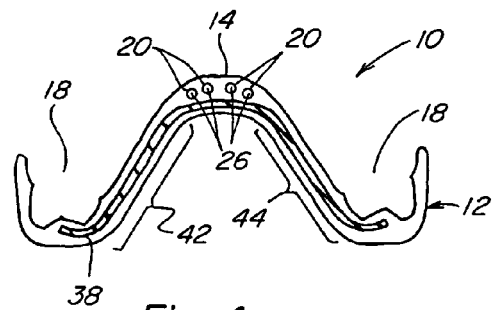
FIG. 4 is a sectional view of the brachytherapy appliance, taken along line 4-4 of FIG. 3.
Figure 4A:
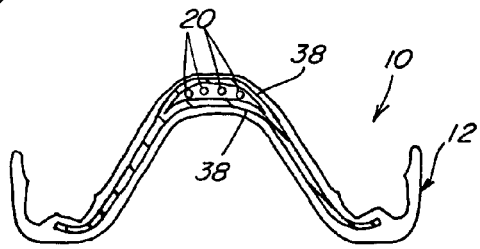
FIG. 4a is a sectional view of the appliance illustrating alternative shielding of the invention.
Figure 4B:
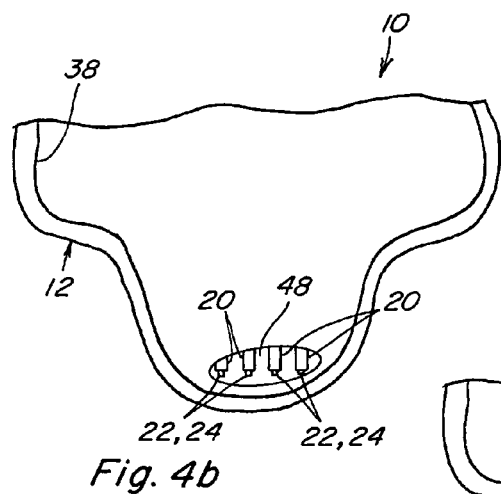
FIG. 4b is a top view of the appliance, illustrating another alternative shielding.
Figure 4C:
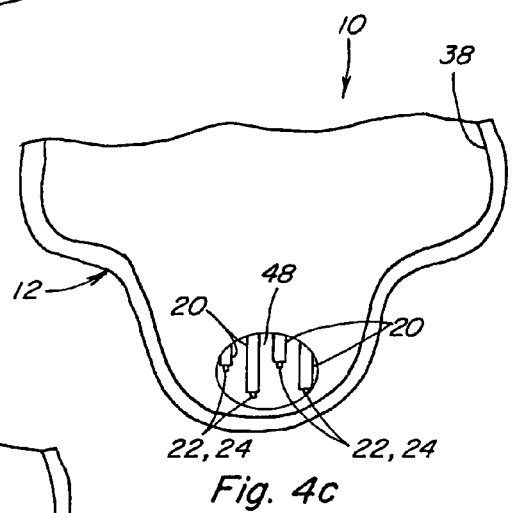
FIG. 4c is another top view of the appliance, illustrating another alternative shielding.
Figure 4D:
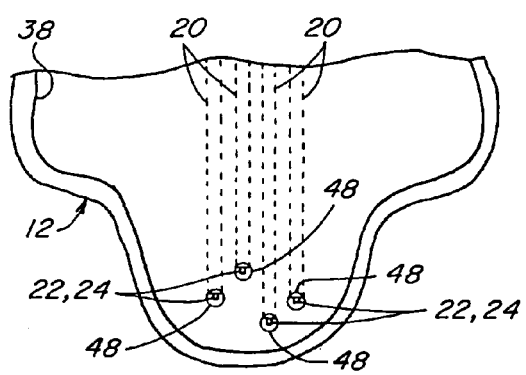
FIG. 4d is a fragmentary top view of the appliance, illustrating still further alternative shielding.
Figure 5A:
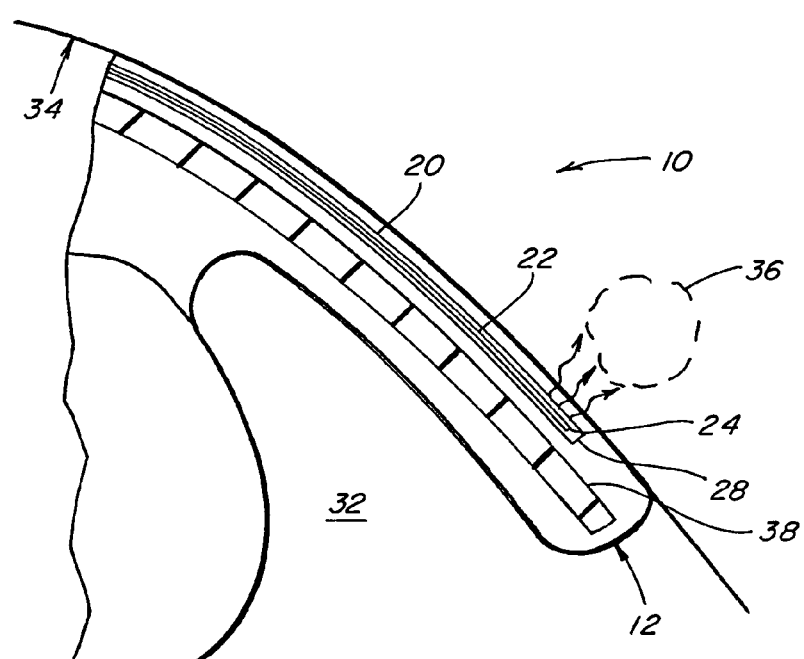
FIG. 5a is an enlarged fragmentary side view of the human head of FIG. 5, showing the appliance in relation to a cancer, and radiation being emitted toward the cancer.

Still further, it is contemplated according to the invention that catheters 20 can be of the same or a different length, for positioning radiation emitting portions of wires, such as tips 24 of wires 22, in desired relation to a cancer for dosing the cancer with radiation, as illustrated in FIGS. 4b, 4c and 4d. For instance, terminal end portions 28 or other radiation positioning portions of a plurality of catheters 20 could be arranged in a generally circular, oval, offset, or other shaped array deemed most effective for dosing a cancer with radiation, as illustrated in FIGS. 4c and 4d. A plurality of catheters 20 can also be arranged in a three-dimensional array, again, such as deemed most effective for dosing a cancer with radiation.

As another feature of the invention, wires 22 and/or catheters 20 can include indicia for indicating when wires 22 are fully received within catheters 20, respectively, for positioning the radiation emitting portions of the wires, such as radioactive tips 24, at the desired position in relation to a cancer. For instance, such indicia can include a mark or markings along the length of a wire 22, such as a dyed or etched spot, notch, or the like, as generally denoted by numerals 46 in FIG. 1, which will match up with an end 30 of a catheter 20 (FIG. 5), such that when the mark or marking is coincident with, or in other predetermined relation with, end 30, a healthcare professional inserting the wire 22 into a catheter 20 will know that the wire is properly and fully positioned within the catheter. The properly positioned wire or wires 22 will then be left in the catheter or catheters 20 for the prescribed time, and then removed when the radiation dose has been delivered. Alternatively, or additionally, a wire or wires 22 could include a hard stop, such as a sharp bend or crease at the location therealong to be coincident with the end 30 of conduit 20, to provide the desired indication of proper positioning.

Referring also to FIGS. 6, 7, 8 and 9, another brachytherapy appliance 50 constructed and operable according to the teachings of the present invention, is shown, like parts of appliance 50 and appliance 10 being identified by like numerals. Brachytherapy appliance 50 is configured for use in an oral cavity of a living body, which, as depicted in FIG. 9, is a human body. Appliance 50 generally includes a body portion 52 which will be at least generally and preferably custom molded to the contours of a region of an oral cavity of a living body. More particularly, body portion 52 is molded to conform to the lower teeth 54, if any, and/or the lower endentulous ridge or arch, thereby forming a recess 56 contoured for cooperatively receiving and releasably attaching to the lower teeth 54, if any, or to the lower edentulous ridge or arch. Body portion 52, like body portion 12, can be molded using common dental molding techniques and commercially available polymeric materials commonly used in the same, such as a well-known, commercially available dental acrylic material such as a methyl methacrylate. Importantly, at least one therapy delivery element is incorporated into appliance 50, which here preferably comprises at least one catheter 20 incorporated in or on body portion 52. Each catheter 20 is preferably adapted for cooperatively receiving and positioning radioactive media in desired relation to a cancer, which media here comprises an elongate wire 22 (illustrated in other Figures) including a radiation emitting portion, which is preferably a radioactive tip of iridium 192, as explained above. Each catheter 20 is essentially a hollow tube defining a passage having at least a terminal end portion 28 which is precisely positioned in relation to body portion 52, such that when a wire 12 is receivable in the passage with radioactive tip 24 located in the terminal end portion 28, tip 24 will be precisely positioned for irradiating a cancer or diseased tissue when appliance 50 is installed in the oral cavity.

The location, size and extent of the cancer will be determined by an oncology professional, and the radiological dosing will be determined by the oncology professional and/or physicist. From that information, the number and position of catheters 20 required will be determined by the professionals. Appliance 50 will be fabricated to include the required number of catheters 20, in the required position or positions, such that the therapy delivering region or regions of the wire or wires inserted into the catheter or catheters will be properly disposed for delivering the contemplated radiation dose to the cancer or diseased tissue. In this embodiment, this will entail the positioning of terminal end portions 28 of the catheters 20 in, or in connection with, molded body portion 52, such that the radioactive tips 24 of the wires when located in the catheters will be positioned for delivery of the required radiation dose to the cancer. Preferably, this will entail the fixed molding in place of catheters 20 within body portion 52, such that terminal end portions 28 will be fixed in location with respect to the cancer or diseased tissue when appliance 50 is installed in the oral cavity. Also preferably, this will entail allowing the extension of opposite ends 30 of catheters 20 from body portion 52, and thus also from the mouth 32 of a person 34 when appliance 50 is installed, as shown in FIG. 9. This will allow a healthcare professional to safely and conveniently insert wires 22 into catheters 20 with body portion 52 installed in the mouth, to position radioactive tips 24 at terminal end portions 28 within catheters 20, for delivering the required radiation dose to a cancer or diseased tissue, such as representative cancer 58, also illustrated in FIG. 9. At the end of the radiation therapy, wires 22 are removed from body portion 52, and body portion 52 removed from the mouth.

As noted hereinabove in relation to appliance 10, radiation emitted by a therapeutic device, such as any of radioactive tips 24 of wires 22, can potentially unintentionally injure or damage noncancerous body parts, tissue, glands and/or organs, such as the teeth, salivary glands, olfactory nerves, taste buds, and the like. To avoid such injury or damage, appliance 50 includes one or more shields, such as a radiation shield 38 as illustrated in FIGS. 8 and 9, in association with body portion 52, positioned or disposed for providing shielding of desired tissue regions, glands, organs, and/or other body parts, from radiation emitted by tips 24. A shield, such as radiation shield 38, can comprise a suitable radiation absorbing or containing material, such as lead. To protect non-diseased body portions, such as the tissue of the inferior and superior regions of the oral cavity, such as the endentulous arch, the tongue, teeth, and the like, located in the vicinity of a shield, such as shield 38, from unhealthy effects from exposure to the material of the shield, the shield is preferably encapsulated by a layer of protective material, for instance, by one or more layers of the polymeric material constituting body portion 52, such as an acrylic or the like. A shield can be encapsulated within body portion 52 when molded, or can be installed on a surface thereof, then coated with the protective layer. Here, for instance, terminal and portions 28 of catheters 20 are disposed in the lateral region of body portion 52, for irradiating a cancer in the cheek region of the oral cavity, as generally illustrated by cancer 58 in FIG. 9. Shield 38 for this location, can cover the region of body portion 52 which will face the healthy tissue to be shielded, generally denoted as region 60 in FIG. 9, to protect the healthy tissue, as well as those portions of the teeth and gums that face and therefore could be injured by subjection to radiation emitted by tips 24 when installed in catheters 20.

Thus, there has been shown and described a novel brachytherapy appliance and method, which overcomes many of the problems and shortcomings set forth above. It will be apparent, however, to those familiar in the art, that many changes, variations, modifications, and other uses and applications for the subject device are possible. All such changes, variations, modifications, and other uses and applications that do not depart from the spirit and scope of the invention are deemed to be covered by the invention which is limited only by the claims which follow.

What is claimed is:

1. A brachytherapy appliance, comprising:

a body portion custom fitted to conform to a region of the oral cavity and configured for inserting into the oral cavity of a living body, the body portion when located both in and out of the cavity including at least one outer concave surface portion at least generally conforming to a convex contour or contours of an interior surface defining at least a portion of the cavity, such that the body portion is insertable into the cavity and retainable in a predetermined position and orientation adjacent to the interior surface by placement of the outer concave surface portion in overlaying generally conforming relation to the convex contour or contours;

at least one catheter in connection with the body portion and having a predetermined portion disposed in fixed relation to the concave surface region so as to be located in a predetermined position and orientation relative to a cancer or diseased tissue in or adjacent to the interior surface when the body portion is retained in the predetermined position adjacent thereto; and an elongate element including a radiation emitting portion, at least a portion of the elongate element including the radiation emitting portion being adapted to be cooperatively received in the catheter to position the radiation emitting portion in predetermined relation to the cancer or diseased tissue when the body portion is retained in the predetermined position, for emitting radiation toward the cancer or diseased tissue, and at least one radiation shield incorporated into at least one portion of the body portion in fixed relation to and substantially larger than the at least one catheter for shielding healthy tissue of the living body from the emitted radiation.

2. The appliance of claim 1, wherein the radiation shield comprises an envelope containing at least a portion of the at least one catheter.

3. The appliance of claim 2, wherein the envelope includes at least one window through which the radiation will be emitted when the radiation emitting portion is positioned in the catheter for emitting the radiation toward the cancer or diseased tissue.

4. The appliance of claim 1, wherein the elongate element comprises a wire having a radiation emitting tip, and the radiation shield includes a window in which the radiation emitting tip will be located when the elongate element is received in the catheter.

5. The appliance of claim 1, comprising a plurality of the catheters and a plurality of the elongate elements having tips which comprise the radiation emitting portions thereof, respectively, the radiation shield being configured such that the tips will be located adjacent to a window of the radiation shield through which the radiation will be emitted when the elongate elements are received in the catheters.

6. The appliance of claim 5, wherein the catheters are arranged in an array within the body portion such that the tips will be arranged in an array within the window of the radiation shield when the elongate elements are received in the catheters.

7. The appliance of claim 1, wherein the predetermined portion of the at least one catheter comprises a terminal end portion thereof.

8. The appliance of claim 1, wherein the at least one catheter comprises a tube.

9. The appliance of claim 1, wherein the body portion is molded to fit contours of an interior surface of an oral cavity, and the at least one radiation shield is configured to generally conform to the contours of the interior surface.

10. The appliance of claim 1, wherein the outer concave surface portion of the body portion conforms to contours of an endentulous arch within an oral cavity, and the at least one radiation shield is configured to conform to at least a portion of the endentulous arch.

11. The appliance of claim 10, wherein the outer concave surface portion of the body portion conforms to contours of teeth located within the oral cavity, and the at least one radiation shield is configured to cover at least a substantial portion of the teeth.

12. A brachytherapy appliance kit, comprising:
a body portion having an outwardly facing concave upper surface portion custom fitted to conform to a convex shape of an endentulous arch region within an oral cavity such that the body portion is insertable into the cavity to position the concave upper surface portion against and in at least generally conforming relation to the endentulous arch region for holding the body portion in a predetermined position and orientation in the cavity, the body portion including at least one conduit defining a passage extending through a portion thereof from an opening disposed so as to be located external to the oral cavity to a predetermined location on or in the body portion positioned so as to be located in the vicinity of a cancer or diseased tissue located in or adjacent to the oral cavity when the body portion is in the predetermined position and orientation in the cavity, and at least one radiation shield incorporated into at least one portion of the body portion; and
a radiation emitting element insertable into the passage through the opening so as to be positionable at the predetermined location on or in the body portion so as to be positioned to emit radiation at the cancer or diseased tissue when the body portion is positioned in the cavity, the at least one shield being positioned in fixed relation to and substantially larger than the at least one conduit for shielding healthy tissue of the living body from the emitted radiation.

13. The brachytherapy appliance kit of claim 12, wherein the radiation emitting element comprises a wire including a radioactive tip.

14. The brachytherapy appliance kit of claim 12, wherein the radiation shield envelopes at least a portion of the passage and includes a window through which the radiation will be emitted when the radiation emitting element is located in the passage.

15. The brachytherapy appliance kit of claim 12, wherein the at least one conduit comprises a tubular catheter.

16. The brachytherapy appliance kit of claim 15, wherein the predetermined location comprises a terminal end portion of the tubular catheter disposed adjacent to a window of the radiation shield.

17. The brachytherapy appliance kit of claim 16, comprising a plurality of the catheters and wherein at least the terminal end portions of the catheters are arranged in a predetermined array disposed adjacent to the window of the radiation shield through which the radiation will be emitted.

18. The brachytherapy appliance kit of claim 15, wherein at least one of the catheter and the radiation emitting element includes indicia for indicating when the radiation emitting element is properly positioned at the predetermined location on or in the body portion.

19. A brachytherapy method, comprising steps of:
providing a unitary body element having a concave surface portion, custom fitted to conform to a surface region of an oral cavity whether the body element is located in the cavity or out of the cavity;
providing a conduit in connection with the body element extending from an opening to a predetermined location on or in the body element positioned so as to be located in the vicinity of a cancer or diseased tissue located in or adjacent to the cavity when the body element is positioned in the cavity with the concave surface portion in conforming relation to the surface region, the conduit being adapted for receiving a radiation emitting element through the opening for positioning the radiation emitting element at the predetermined location;
providing a radiation shield incorporated in a portion of the body element in fixed relation to and substantially larger than the conduit;
positioning the body element in the cavity to position the concave surface portion in conforming relation to the surface region; and
inserting a radiation emitting element through the opening and into the conduit so as to be positioned at the predetermined location for emitting radiation at the cancer and so as to be in fixed relation to the radiation shield such that the radiation shield will shield adjacent healthy tissue from the emitted radiation.

20. The method of claim 19, wherein the surface portion of the body element conforms to a shape of an upper surface region of a human oral cavity.

21. The method of claim 19, wherein the radiation is emitted through a window of the radiation shield.

22. The method of claim 19, wherein the radiation shield completely ensconces the conduit except for a window through which the radiation will be emitted.

* * * * *